United States Patent
Mo et al.

(10) Patent No.: US 6,185,465 B1
(45) Date of Patent: Feb. 6, 2001

(54) VAGINAL ELECTRODE FOR URINARY INCONTINENCE TREATMENT

(76) Inventors: Seung Kee Mo, #107-703 Kangbyun Apt., Manyun-dong Seoh-ku, Taejon 302-150 (KR); Soo Yeol Lee, #101-1406 Samil Apt., Childeum-dong Choongjoo-shi, Choongheongbook-do 380-220 (KR)

(*) Notice: Under 35 U.S.C. 154(b), the term of this patent shall be extended for 0 days.

(21) Appl. No.: 09/251,171

(22) Filed: Feb. 17, 1999

(30) Foreign Application Priority Data

Feb. 25, 1998 (KR) .................................................. 98-5998
Jul. 7, 1998 (KR) .................................................. 98-27301

(51) Int. Cl.⁷ .............................. A61N 1/00; B29C 37/02
(52) U.S. Cl. ............................................. 607/138; 264/250
(58) Field of Search ................................ 607/40, 41, 138

(56) References Cited

U.S. PATENT DOCUMENTS

| | | | |
|---|---|---|---|
| D. 348,934 | 7/1994 | Johnson et al. | D24/187 |
| D. 360,944 | 8/1995 | Juma | D24/124 |
| D. 371,200 | 6/1996 | Maurer et al. | D24/187 |
| 4,612,939 | 9/1986 | Robertson | 128/774 |
| 4,785,828 | 11/1988 | Maurer | 128/744 |
| 4,873,996 | 10/1989 | Maurer | 128/844 |
| 4,881,526 | 11/1989 | Johnson et al. | 128/24.5 |
| 4,909,263 | 3/1990 | Norris | 128/788 |
| 5,010,895 | 4/1991 | Maurer et al. | 128/788 |
| 5,046,511 | 9/1991 | Maurer et al. | 128/788 |
| 5,314,465 | 5/1994 | Maurer et al. | 607/138 |
| 5,370,671 | 12/1994 | Maurer et al. | 607/41 |
| 5,376,206 | 12/1994 | Maurer et al. | 156/242 |
| 5,385,577 | 1/1995 | Maurer et al. | 607/41 |
| 5,476,434 | 12/1995 | Kalb et al. | 600/30 |
| 5,516,396 | 5/1996 | Maurer et al. | 156/242 |
| 5,562,717 | 10/1996 | Tippey et al. | 607/41 |
| 5,759,471 * | 6/1998 | Malewicz | 607/138 |

* cited by examiner

Primary Examiner—Scott M. Getzow
(74) Attorney, Agent, or Firm—Sheridan Ross P.C.

(57) ABSTRACT

An electrode for insertion into a body cavity during medical treatment, for example, urinary incontinence treatment, may be inserted into a body cavity and used in contact with a muscular surface, and through which at least one electrical signal is applied to the muscular surface under a control of a controller and at least one EMG signal is detected from the muscular surface. The electrode includes: a rod-shaped main body composed of non-conductive material; a plurality of ring-shape conductive bands each of which is disposed apart from one another along a longitudinal axis of the rod-shaped main body; a plurality of ring-shaped metal bands each of which is buried within one of the plurality of ring-shape conductive bands, respectively; and a plurality of electrical lines each of which has one end connected to a corresponding one of the plurality of ring-shaped metal bands and buried within the rod-shaped main body and the other end extended through a rear side of the rod-shaped main body to be electrically coupled to the controller. The main body and the ring-shaped conductive bands are made of non-conductive silicon and conductive silicon, respectively. Also, the main body is formed in a unit by molding process so that there is no hollow space within it. The ring-shaped conductive bands can be formed on the inner and the outer surfaces of the ring-shaped metal bands by a molding process using conductive silicon. This electrode feeds excellent when inserted into a body cavity, is waterproof, durable and easy to manufacture. Moreover, the cost of manufacturing according to the present invention can be remarkably reduced.

28 Claims, 13 Drawing Sheets

VAGINAL ELECTRODE FOR URINARY INCONTINENCE TREATMENT

BACKGROUND OF THE INVENTION

The present invention relates to an electrode for insertion into a body cavity, and in particular, to an electrode for insertion into a vagina for urinary incontinence treatment.

Urinary incontinence is a common problem throughout the world and is particularly prevalent in the female population and in the aged. A large number of women suffer from urinary incontinence due to childbirth or general deterioration of body structures as an aging process and so on. It is known that about 20–30% of women over 50 years old suffers from urinary incontinence. Resulting from urinary incontinence is embarrassment, discomfort and distress, loss of sleep and the necessity for large monetary disbursements by the patients for absorbent pads, diapers, rubber sheeting and for cleaning of soiled clothing.

These days the treatment for urinary incontinence includes surgery, physical rehabilitation and drug therapy.

The surgery treatment methods are invasive and thus most patients hesitate to choose this option over others. In addition, the drug therapies are known to provide very limited effectiveness. However, treatment for urinary incontinence is viewed differently by society as many non-invasive and non-pharmaceutical treatment methods are being introduced lately. Among such treatment methods, a biofeedback therapy and a neuromuscular electrical stimulation method are most commonly recognized as major treatment methods. These treatments have been proven very effective, safe to use and relatively inexpensive. In biofeedback therapy, repetitive contractions of pelvic floor muscles improve the strength of the pelvic floor muscles. Neuromuscular electrical stimulation method applies current pulses to pelvic floor muscles so that the motor nerve fibers are electrically stimulated. For more effective treatment for urinary incontinence, it is desirable that both the biofeedback and neuromuscular electrical stimulation methods are performed at the same time, rather than one of them being independently performed.

For the sake of performing such treatment methods, an electrode is needed for delivering electrical pulses to a vaginal muscle. This electrode is generally made in cylindrical shape suitable for insertion into a vagina. One example of this cylinder-shaped electrode is disclosed in U.S. Pat. No. 5,199,443. Referring to this, the electrode is formed cylindrically, non-conductive polymer bands and conductive polymer bands alternatively disposed. Here, the conductive polymer band is used to deliver electrical signals to the vaginal muscle or detect an EMG signal from the vaginal muscle. Accordingly, the conductive polymer band is necessary to be coupled to an external device that generates electrical signals and this connection is made with sockets and electrical wires. Although the conductive polymer bands are in general more comfortable to insert into the vagina than metal bands, the conductivity of the polymer band is much lower than that of the metal band. Thus, to improve the transfer characteristics of the electrical signal, multiple band-type of metal rings are inserted at the inner circumference of the conductive polymer bands. More specifically, in the electrode disclosed in U.S. Pat. No. 5,199,443, the diameter of the metal rings are slightly larger than the inner diameter of the conductive polymer band and the metal rings are also discontinuous, which gives the metal rings resilient force. This resilient force of the metal rings causes the electrical/mechanical connection to be supported between the conductive polymer bands and the metal ring.

However, problem exists in that this connection is very week against an external mechanical impact because the inner part of the electrode is hollow, so that making such electrode is very little plausible. Moreover, even though the electrode is manufactured, because the electrode should be very frequently inserted into the vagina, the conductive bands and the metal rings are likely to become electrically disconnected by mechanical impact accompanied with the insertion.

In addition, for such electrodes, the front end and the rear end are separately formed in cap shape and then coupled to the main member, for example, by adhesives or the like, which results in reducing the durability at the cap connection portion. Further, since the electrode for insertion into a vagina requires to be very frequently washed, if any crevice at the cap connection portions, water and disinfectant are apt to permeate through the crevice. Also, the hollow of the electrode decreases the durability as well as increases the possibility of an electrical shock accident in case of the water leakage through the cap crevice.

SUMMARY OF THE INVENTION

Accordingly, the object of the present invention is to provide an electrode for insertion into a body cavity during medical treatment, which has high durability and no water-leakage possibility, and is suitable for easy manufacturing.

Another object of the present invention is to provide an electrode for insertion into a body cavity during medical treatment, which is comfortable & convenient to use.

Still another object of the present invention is to provide a manufacturing method of such electrodes.

In order to accomplish the above objects, according to one aspect of the present invention, there is provided an electrode for medical treatment purposes which may be inserted into a body cavity and used in contact with a muscular surface, and through which at least one electrical signal is applied to the muscular surface under a control of a controller and at least one EMG signal is detected from the muscular surface, the electrode comprising: a rod-shaped main body composed of non-conductive material; a plurality of ring-shaped conductive bands each of which is disposed apart from one another along a longitudinal axis of the rod-shaped main body; a plurality of ring-shaped metal bands each of which is buried within one of the plurality of ring-shaped conductive bands, respectively; and a plurality of electrical lines each of which has one end connected to a corresponding ring-shaped metal band and buried within the rod-shaped main body, and the other end extended through a rear side of the rod-shaped main body to be electrically coupled to the controller.

According to one preferred embodiment, the rod-shaped main body is made of non-conductive silicon. The ring-shaped conductive bands are made of conductive silicon. Each of the ring-shaped conductive bands has been formed while projecting outside in comparison with adjacent parts of the main body. Specifically, each of the ring-shaped conductive bands has a radius larger than that of an outer surface of the main body by 0.1 to 0.3 mm. Preferably, the electrode may also have a missing preventive projecting part in the middle of the rod-shaped main body and at least one (preferably one) of the ring-shaped conductive bands is located on the missing preventive projecting part. In this case, the ring-shaped conductive band located on the projecting part may be coupled to a ground potential.

Also, the conductivity of the conductive silicon is preferably in the range of 5–20 Ω.cm. The width of the ring-shaped conductive band is preferably in the range of 3–15 mm. The conductive bands are separately disposed from each other by 2–20 mm. Here, the electrode may be in general a vaginal electrode for treatment of urinary incontinence treatment. For this, the solidity of the rod-shaped of main body is preferably in the range of 30–80 Shore A. Also, the diameter of the ring-shaped main body is 15–30 mm and the length is 80–135 mm. The front side of the main body is preferably dome-shaped.

In addition, the electrode may further comprises an electrical line protecting member at the rear side of the rod-shaped main body and a insertion-depth control member which can be coupled to the rear side of the main body so as to control the depth of insertion into a body cavity.

In accordance with another aspect of the present invention, there is provided an electrode for medical treatment purposes which may be inserted into a body cavity and used in contact with a muscular surface, and through which at least one electrical signal is applied to the muscular surface under a control of a controller and at least one EMG signal is detected from the muscular surface, the electrode comprising: a rod-shaped main body composed of non-conductive material; a plurality of ring-shaped conductive bands each of which is disposed apart from one another along the longitudinal axis of the rod-shaped main body; and a plurality of electrical lines each of which has one end connected to a corresponding one of the plurality of ring-shaped conductive bands and buried within the rod-shaped main body and the other end extended through a rear side of the rod-shaped main body to be electrically coupled to the controller. Here, the rod-shaped main body may be made of plastic material and the ring-shaped conductive bands may be made of metal.

According to still another aspect of the present invention, there is provided a manufacturing method of an electrode for insertion into a body cavity during medical treatment, comprising the steps of: forming a plurality of ring-shaped metal bands; forming a plurality of ring-shaped conductive bands surrounding the inner and/or outer circumferences of the plurality of ring-shaped metal bands by molding process using conductive material; soldering a plurality of electrical lines to the plurality of ring-shaped metal bands, respectively; disposing the plurality of conductive bands including the ring-shaped metal bands coupled to the electrical lines in the longitudinal direction one a rod-shape matrix and arranging the electrical lines such that one ends of the electrical lines are extended through one end of the rod-shaped matrix to outside of the matrix; and molding the non-conductive material in between and inside of the ring-shaped conductive bands on the matrix, so as to form the electrode. The plurality of ring-shaped conductive bands is molded by using conductive silicon and the non-conductive material is non-conductive silicon.

According to one preferred embodiment of the present invention, the manufacturing method of an electrode for insertion into a body cavity during medical treatment, comprises the steps of: forming a plurality of ring-shaped metal bands; soldering a plurality of electrical lines to the plurality of ring-shaped metal bands, respectively; disposing the plurality of metal bands coupled to the electrical lines in the longitudinal direction on a rod-shape matrix and arranging the electrical lines such that one ends of the electrical lines are extended through one end of the rod-shaped matrix to outside of the matrix; and molding non-conductive material in between and inside of the ring-shaped conductive bands on the matrix. In this case, the conductive material may be conductive silicon and the non-conductive material may be formed of plastic.

According to another preferred embodiment, the manufacturing method of an electrode for insertion into a body cavity includes the steps of: forming a plurality of ring-shaped metal bands; forming a plurality of ring-shaped conductive bands by molding conductive material surrounding the inner and outer circumferences of the ring-shaped metal bands; soldering a plurality of electrical lines to the ring-shaped metal bands, respectively; molding non-conductive material into a supporting member; inserting the supporting member into the plurality of ring-shaped conductive bands including the ring-shaped metal bands coupled to the electrical lines such that the ring-shaped conductive bands are disposed apart from one another; mounting the supporting member inserted into the plurality of conductive bands on a rod-shaped matrix and arranging the electrical lines such that one ends of the electrical lines are extended through one end of the rod-shaped matrix to outside of the matrix; and molding non-conductive material in between and inside of the ring-shaped conductive bands on the matrix. For this method, the conductive material may be conductive silicon and the non-conductive material may be non-conductive silicon.

According to still another preferred embodiment, the manufacturing method of an electrode for insertion into a body cavity includes the steps of: forming a plurality of ring-shaped metal bands; forming a plurality of ring-shaped conductive bands by molding conductive material surrounding the inner and outer circumferences of the ring-shaped metal bands; soldering a plurality of electrical lines to the ring-shaped metal bands, respectively; molding a first non-conductive material into a first and a second supporting members, wherein the first and the second supporting members have structures suitable for connection to each other and the first supporting member includes an electrical line guide opening; inserting the second supporting member into the plurality of ring-shaped conductive bands including the ring-shaped metal bands coupled to the electrical lines such that the ring-shaped conductive bands are disposed apart from one another; making the electrical lines pass through the electrical line guide opening of the first supporting member; coupling the first and the second supporting members together; mounting the resulting produce on a rod-shaped matrix; and molding a second non-conductive material in between and inside of the ring-shaped conductive bands in the matrix, so as to form the electrode. Here, the first and second non-conductive materials are the same materials, for example, non-conductive silicon. Preferably, the first and the second non-conductive materials are non-conductive silicon.

BRIEF DESCRIPTION OF THE DRAWINGS

For more complete understanding of the present invention and the advantages thereof, reference is now made to the following description taken in conjunction with the accompanying drawings in which.

DETAILED DESCRIPTION OF THE PRESENT INVENTION

Hereafter explained in details is the invention referring to the accompanying drawings.

The electrode for insertion into a body cavity according to the present invention is generally inserted into a body cavity for medical treatment. There are two purposes of electrode for insertion into a body; one is to apply electrical stimulation signals to the muscle within the body cavity, and the other is to detect EMG signals from the muscle. In addition, it is used to detect the EMG signals as a reaction to an electrical stimulation current signal applied to the muscle. Applying electrical stimulation signals to a body surface is called neuromuscular electrical stimulation method, and the medical treatment using EMG signals as a reaction to the stimulation is called biofeedback method. The most common examples of electrodes for insertion into a body cavity are rectal and vaginal electrodes.

Although the present invention has been described with reference to the vaginal electrode for the convenience of explanation as an example, those skilled in the art will appreciate that modifications and alternations may be made without departing from the spirit and scope of the invention.

Figure 1:
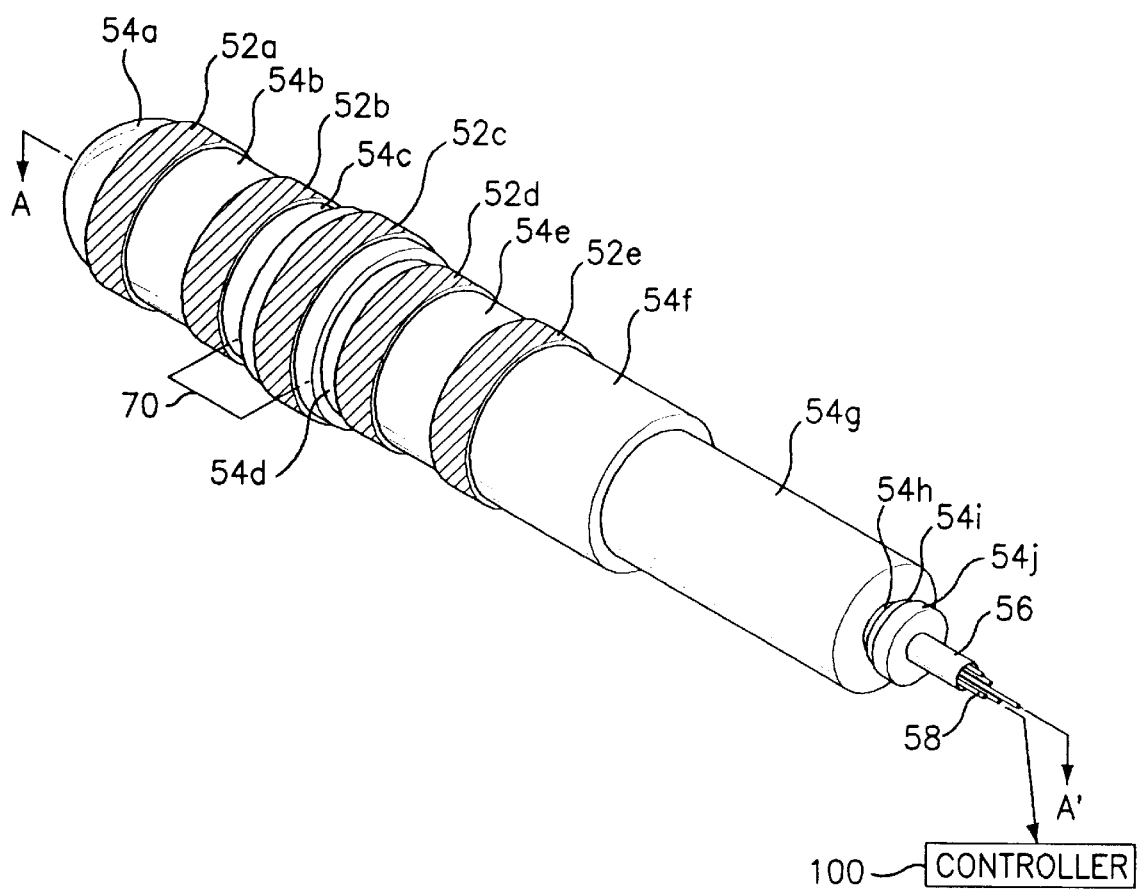
FIG. 1 is a perspective view of a first embodiment of an electrode for insertion into a body cavity in accordance with the present invention.

FIG. 1 is a perspective view of a first embodiment of an electrode for insertion into a body cavity in accordance with the present invention.

Referring to FIG. 1, the main body 54a, 54b, 54c, 54d, 54e, 54f, 54g, 54h, 54i, 54j consisting of electrically non-conductive material is rod-shaped overall. The front portion 54a of the rod-shaped main body is dome-shaped for easy insertion into the vagina. In addition, there is a projecting part 70 in the middle of the rod-shaped main body, which is larger in diameter than the rest of the main body, preventing dislocation of the electrode. This projecting part 70, while the electrode is inserted in the vagina, prevents the electrode from being dislocated or slipping out by a mechanical impact of the patient's activity or an external cause. Thus an advantage lies in that the patients can move and do other works freely while being treated for urinary incontinence by the present invention.

Multiple ring-shaped conductive bands 52a, 52b, 52c, 52d, 52e are formed on the rod-shaped main body. In FIG. 1, although the number of ring-shaped conductive bands 52a, 52b, 52c, 52d and 52e is 5, at least two conductive bands can be formed.

In case of five ring-shaped conductive bands being formed, one of them is used for supplying a ground potential, the others in pairs used either for applying appropriate electrical stimulation signals for urinary incontinence treatment or for detecting EMG signals. At this time, the ring-shaped conductive band 52c on the above-mentioned missing preventive projecting part 70 can be used as such a ground potential node.

In addition, it is desired that the ring-shaped conductive bands 52a, 52b, 52c, 52d, 52e be larger in diameter than the adjacent non-conductive regions. The ring-shaped conductive bands 52a, 52b, 52c, 52d, 52e can be projected by 01–0.3 mm in comparison with the adjacent non-conductive regions. This is in order to prevent the non-conductive materials from covering the conductive bands during the molding process.

In the first embodiment shown in FIG. 1, the rear part 54h, 54i, 54j of the main body is increasing in diameter. This is for placing an electrical line protector 92 described below with reference to FIG. 8, and is also formed by a molding process. The step-down between the portions 54f and 54g of the main body also helps insertion with ease and comfort.

Here, in case of the electrode shown in the drawing being a vaginal electrode, it is preferable to generally have the diameter of 15–30 mm and the length of 80–135 mm. However the diameter and the length of the electrode might vary depending on demography. The width of the above-mentioned ring-shaped conductive bands may desirably range from 3 to 15 mm, and the bands may be disposed apart from each other by 2–20 mm.

The non-conductive parts 54a, 54b, 54c, 54d, 54e, 54f, 54g, 54h, 54i, 54j of the main body, might be made of solid materials such as plastic, nylon resin or the like. In this case, due to its solidity, an advantage lies in that the main body can firmly support the ring-shaped conductive bands mechanically.

According to another embodiment, the non-conductive parts 54a, 54b, 54c, 54d, 54e, 54f, 54g, 54h, 54i and 54j are made of non-conductive silicon and the conductive bands 52a, 52b, 52c, 52d and 52e are made of conductive silicon. The conductivity of the conductive silicon should be similar to that of muscles which is 5–10 Ω.cm to prevent the current from being concentrated on a certain area, which might be painful to the patient.

Such conductive silicon may be manufactured by adding carbon to silicon or may be purchased as a product sold under the name of Rc-1516 by Rhone-Poulenc Company.

When the conductive parts 52a, 52b, 52c, 52d, 52e are made of conductive silicon, its conductivity is remarkably lower than metallic materials. Thus it is desirable to use current-driven amplifier so that the input resistance of the instrumentation amplifier is more than a couple of hundred MΩ.cm for electrical stimulation and EMG biofeedback measurement.

Also, if the main body is formed using non-conductive silicon and the ring-shaped conductive bands are formed using conductive silicon, for the sake of the patient's comfort, the solidity of the electrode may be 30–80 Shore A.

As shown in FIG. 1, according to the present invention, the main body are not formed separately by parts, but formed as one unit by a molding process. Thus an advantage lies in that the unit is highly waterproof while being washed.

Figure 2:
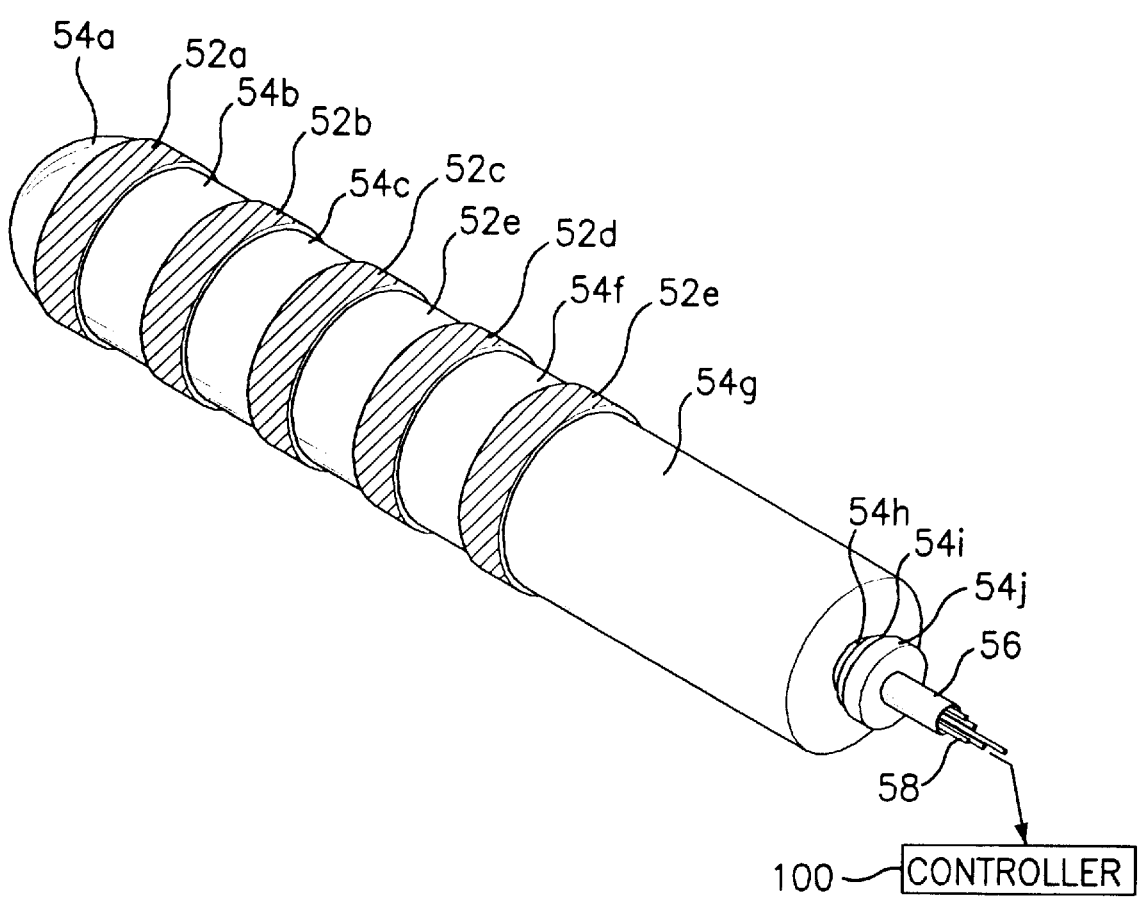
FIG. 2 is a perspective view of a second embodiment of an electrode for insertion into a body cavity.

FIG. 2 is a perspective view of a second embodiment of an electrode for insertion into a body cavity. The same parts with those of FIG. 1 have the same reference numerals and the description thereof will be omitted.

The electrode for insertion into a body cavity shown in FIG. 2, different from FIG. 1, does not have a projecting part 70 in the middle of the main body.

The ring-shaped conductive bands shown in FIGS. 1 and 2 are electrically coupled to an external controller 100. Electrical stimulation is applied to the muscle under the control of the external controller and/or EMG signals captured from the muscle are delivered to the controller 100. In FIG. 2, the structure of the electrical connection between the ring-shaped conductive bands and the controller 100 is described in conjunction with the FIGS. 3 to 5.

Figure 3:
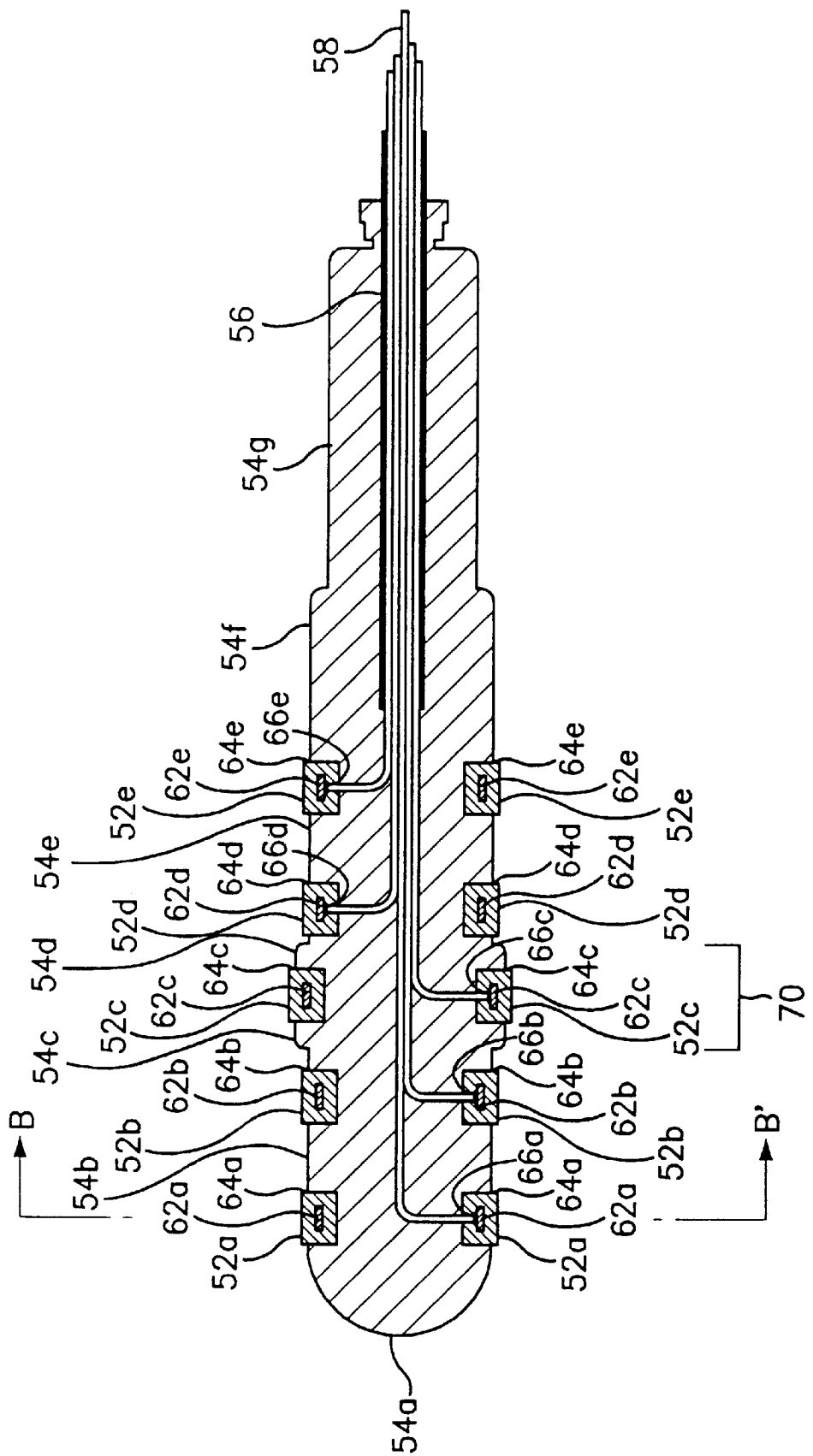
FIG. 3 is a sectional view of a first embodiment of the electrode taken along line A–A' of FIG. 1.
Figure 4:
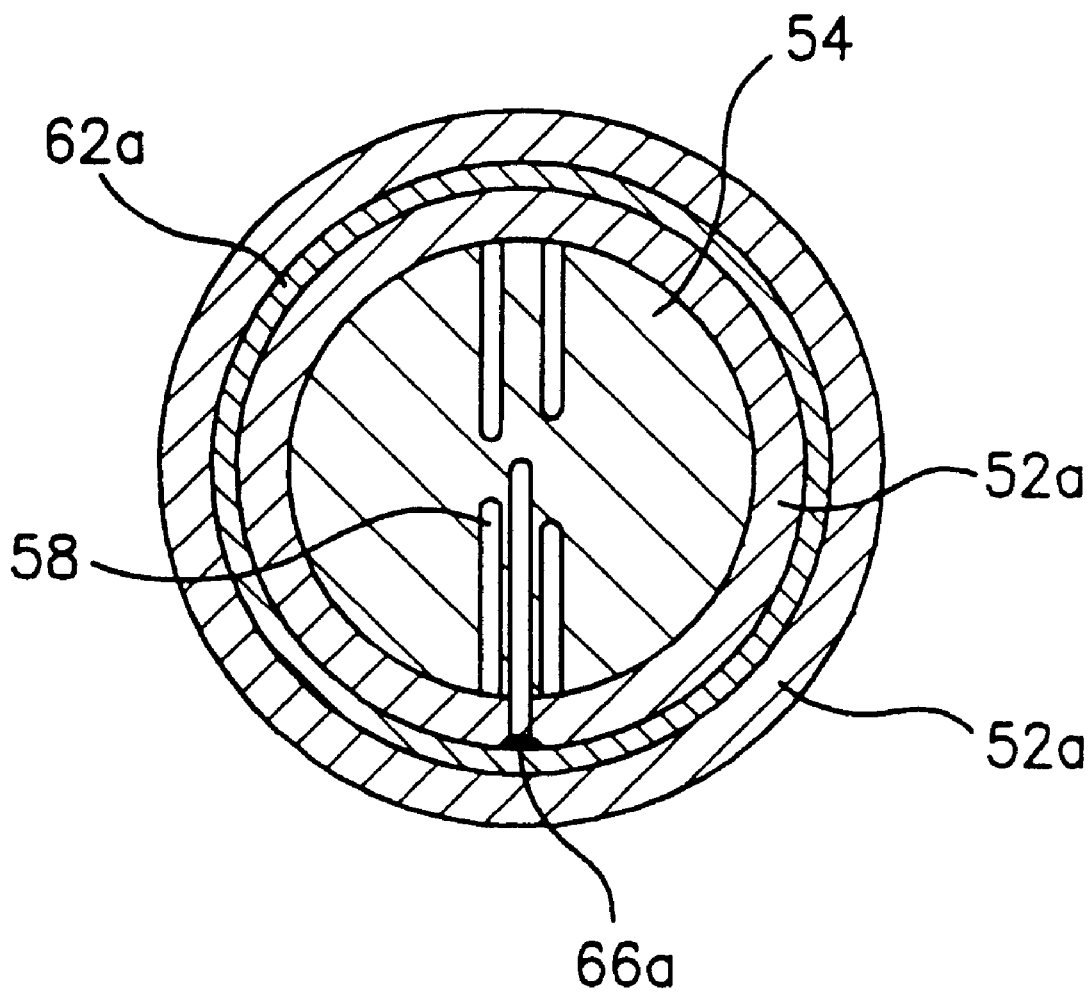
FIG. 4 is a sectional view of the electrode shown in FIG. 3 taken along line B–B'.

FIG. 3 is a sectional view of a first embodiment of the electrode taken along line A–A' of FIG. 1; and FIG. 4 is a sectional view of the electrode shown in FIG. 3 taken along line B–B'. In FIGS. 3 and 4, the same parts with those of FIG. 1 have the same reference numerals and the description thereof will be omitted.

Referring to FIGS. 3 and 4, a plurality of ring-shaped metal bands 62a, 62b, 62c, 62d, 62e are embedded inside the ring-shaped conductive bands 52a, 52b, 52c, 52d, 52e, respectively. In FIG. 3, the ring-shaped metal bands 62a, 62b, 62c, 62d, 62e are embedded by the ring-shaped conductive bands 52a, 52b, 52c, 52d, 52e, respectively. These ring-shaped metal bands 62a, 62b, 62c, 62d, 62e are connected to electrical lines 58 by solders 661, 66b, 66c, 66d, 66e. Five electrical lines 58 are covered by a wiring cable 56 and are extended through the rear side of the main body to the outside so as to be coupled to the controller. Also, in FIG. 3, the reference numerals 64a, 64b, 64c, 64d, 64e show that the ring-shaped conductive bands 52a, 52b, 52c, 52d, 52e are projecting compared to the adjacent main body parts 54a, 54b, 54c, 54d, 54e, 54f.

Figure 5:
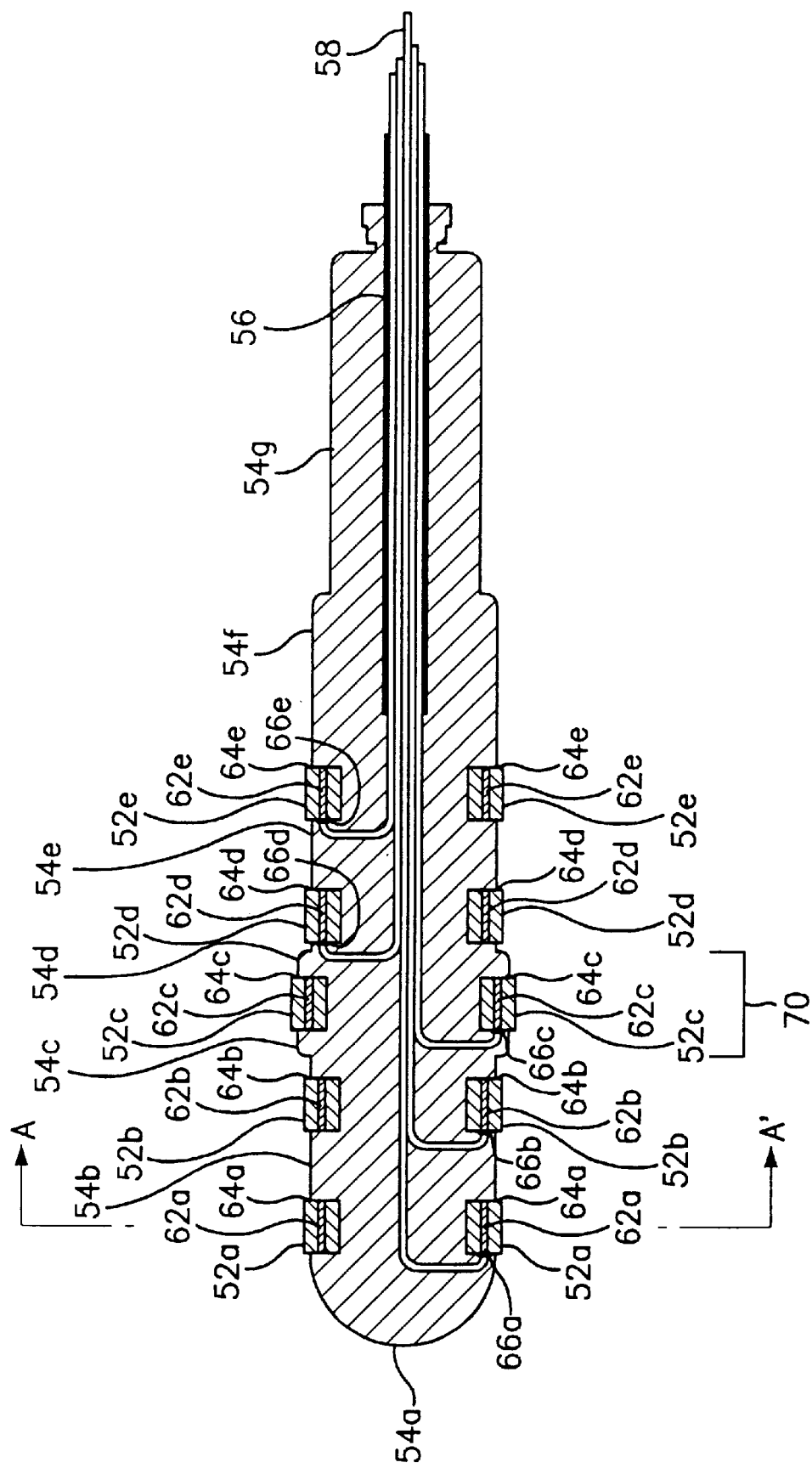
FIG. 5 is a sectional view of a second embodiment of the electrode taken along line A–A' of FIG. 1.

FIG. 5 is a sectional view of a second embodiment of the electrode taken along line A–A' of FIG. 1. Only the inner and outer circumferences of the ring-shaped metal bands 62a, 62b, 62c, 62d, 62e are covered by the ring-shaped conductive bands 52a, 52b, 52c, 52d, 52e. Such a structure has an advantage in that soldering of the electrical lines to the metal bands is accomplished easily.

As seen in FIGS. 3 to 5, the ring-shaped metal bands 62a, 62b, 62c, 62d, 62e are molded and embedded in the ring-shaped conductive bands 52a, 52b, 52c, 52d, 52e, thus the coherence of the two is excellent. Therefore, the connections between the ring-shaped conductive bands and the ring-shaped metal bands can not be separated even by a mechanical impact of the patient's activity or an external cause.

In addition, the main body 54a, 54b, 54c, 54d, 54e, 54f, 54g, 54h, 54I, 54j of the electrode for insertion into a body cavity according to the present invention is formed as one unit with non-conductive materials such as non-conductive silicon. Namely, inside the ring-shaped conductive bands are filled with the non-conductive materials. This structure of the body can be formed by a silicon molding process and thus the coherence of the main body and the ring-shaped conductive bands 52a, 52b, 52c, 52d, 52e is excellent and the manufacturing process becomes very easy. In addition, because inside the ring-shaped conductive bands is filled with silicon that forms the main body and the electrical lines are fixed in place by the non-conductive silicon, the connections between the electrical lines and the ring-shaped metal bands are very firm and unbreakable by a mechanical impact.

Hereafter explained in details is the manufacturing process of the electrode for insertion into a body cavity.

Figure 6A:
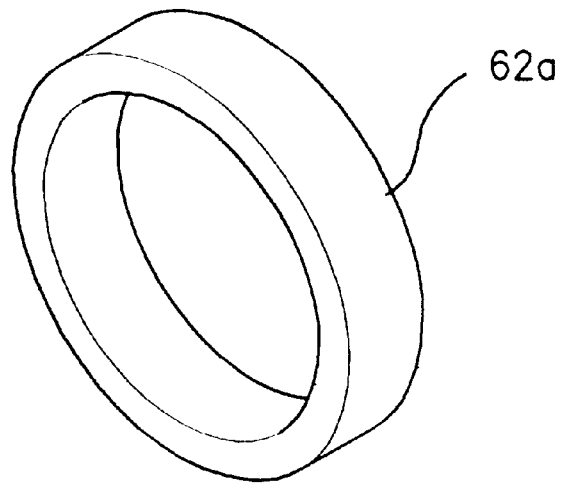
FIGS. 6A–6C illustrate an exemplary manufacturing method of the electrode for insertion into a body cavity.
Figure 6B:
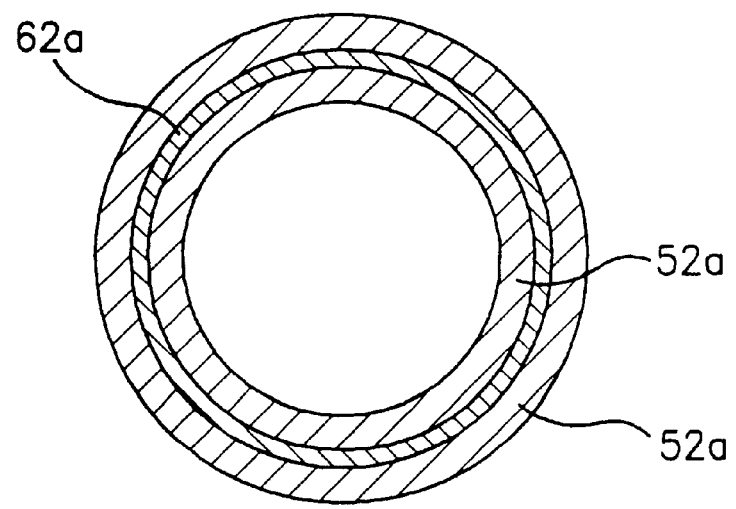
Figure 6C:
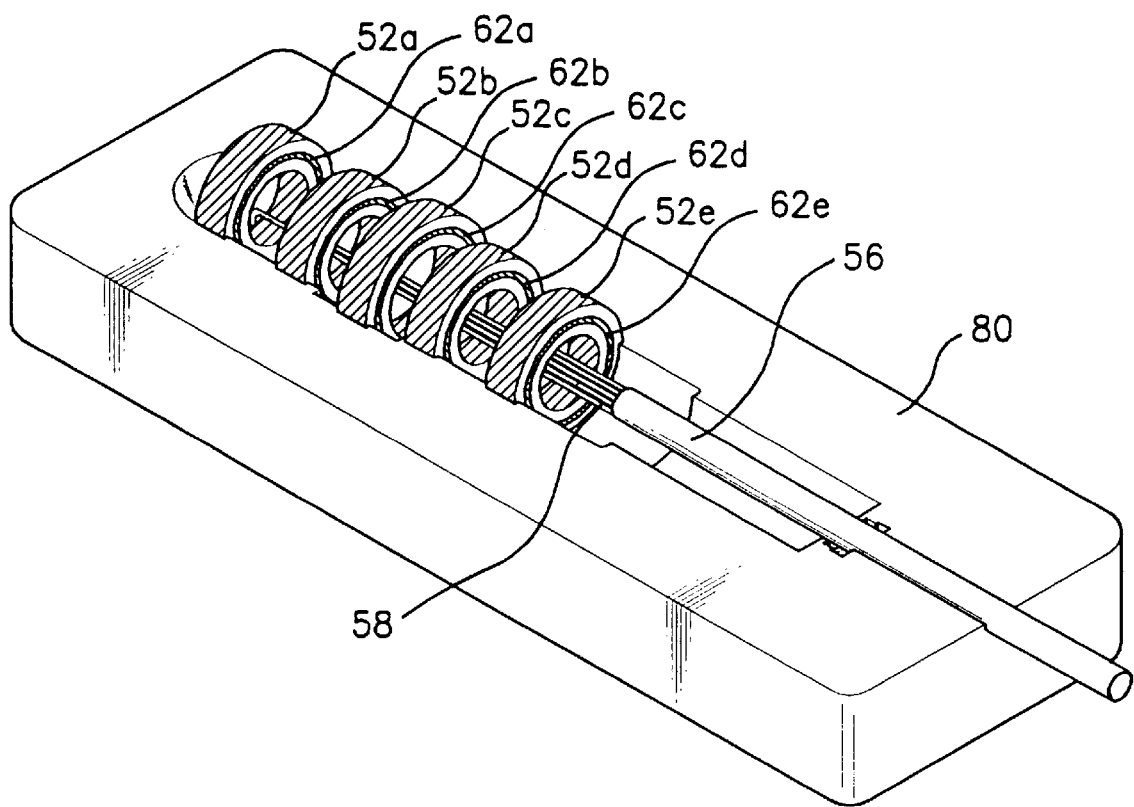

FIGS. 6A to 6C are diagrams of an exemplary manufacturing method of the electrode for insertion into a body cavity.

Referring to FIG. 6A, pluralities of ring-shaped metal band 62a are formed. It is desirable that the width of the ring-shaped metal band 62a be the slightly smaller than that of the ring-shaped conductive silicon band 52a. Also the diameter of the ring-shaped metal band 62c placed in the projecting part 70 is desirably a little larger than the diameter of the rest of the metal bands. After mounting the metal bands in the ring-shaped matrix, ring-shaped conductive bands are molded on the interior and exterior circumferences of the metal bands using conductive materials such as conductive silicon, as shown in FIG. 6B. Then the ring-shaped metal bands inside the plurality of ring-shaped conductive bands 52a, 52b, 52c, 52d, and 52e are connected by soldering to the corresponding electrical line 58.

Then, as shown in FIG. 6C, the ring-shaped conductive bands 52a, 52b, 52c, 52d, 52e are disposed apart from each other in the longitudinal direction of the rod-shaped main body matrix and the electrical lines are also disposed such that one end thereof, which is to be coupled to the controller, is extended through the rear part of the rod-shaped matrix to the outside. Subsequently, as shown in FIG. 6C, the main body is molded in a rod-shaped matrix 80 using non-conductive silicon for example.

Figure 7A:
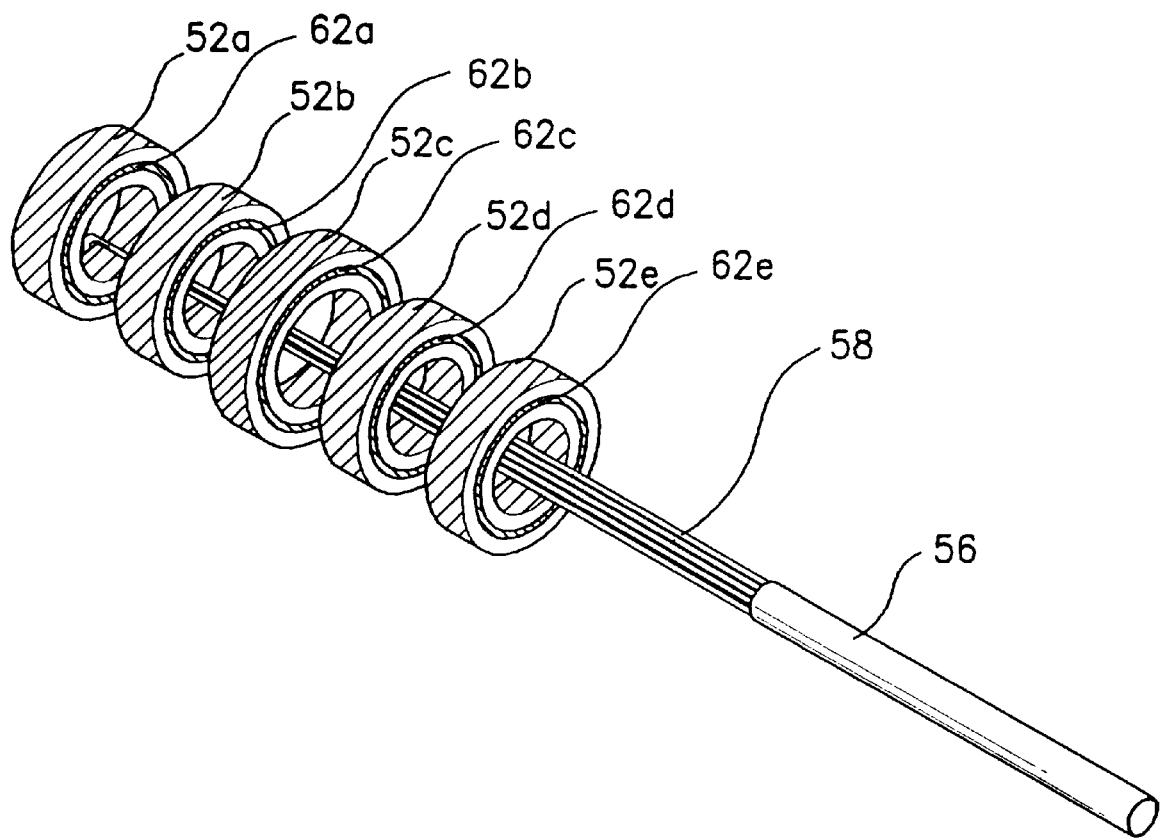
FIGS. 7A–7D are diagrams for showing another exemplary manufacturing method of the electrode for insertion into a body cavity.

FIGS. 7A to 7D are drawings for illustrating another manufacturing method of the electrode for insertion into a body cavity according to another embodiment of the present invention. According to this manufacturing method, the ring-shaped metal bands 62a, 62b, 62c, 62d, 62e and ring-shaped conductive bands 52a, 52b, 52c, 52d, 52e surrounding the ring-shaped metal bands are sequentially formed as the same method described in FIGS. 6A to 6B. Then the ring-shaped metal bands 62a, 62b, 62c, 62d, 62e are connected the corresponding electrical lines inside the cable 56 by soldering as seen in FIG. 7A.

Figure 7B:
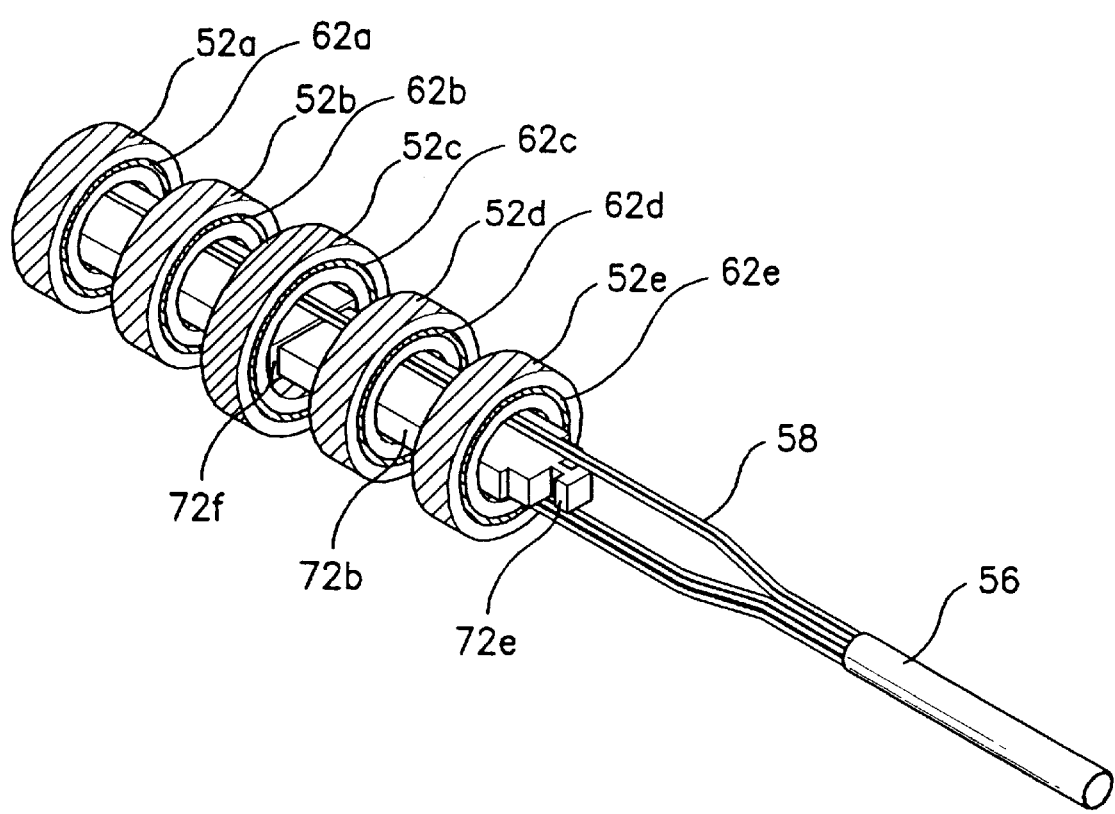
Figure 7C:
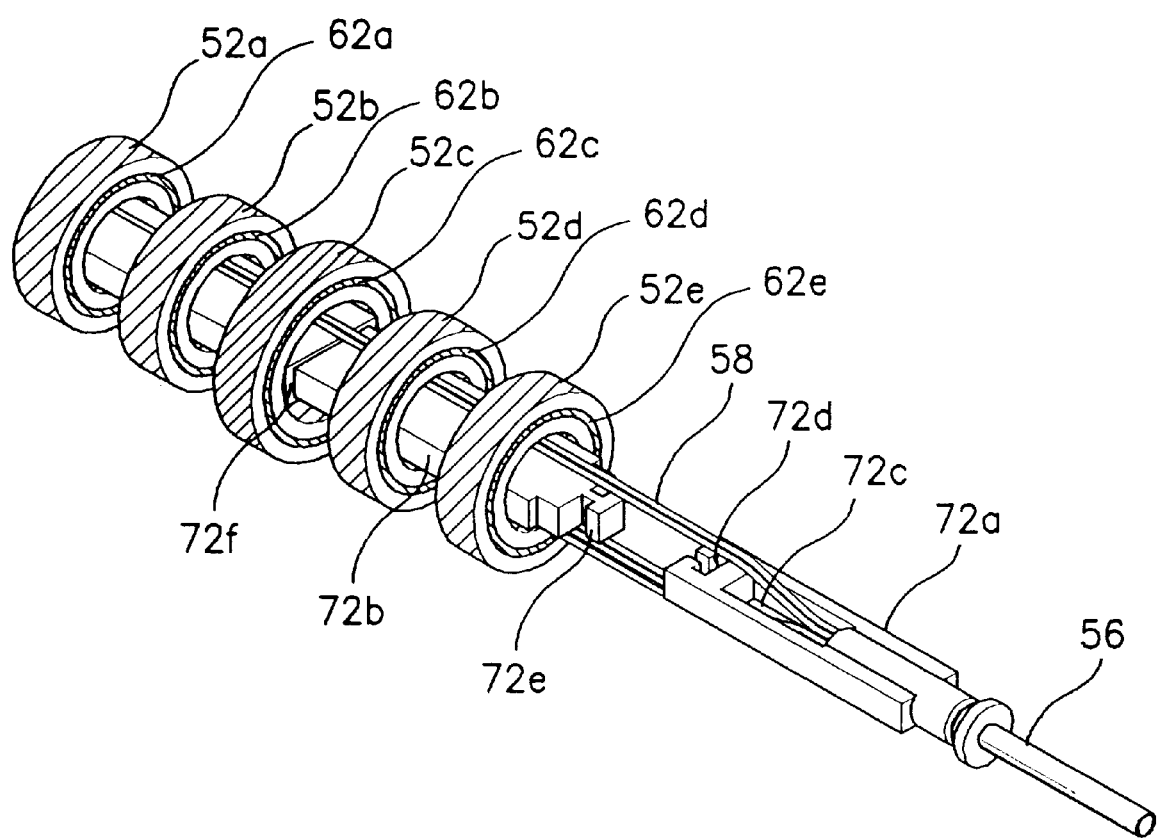

Then, as shown in FIGS. 7B and 7C, a first and a second supporting members 72a and 72b are made by a molding process. The first supporting member 72a and the second supporting member 72b should be made of non-conductive materials, for example non-conductive silicon or plastic, and may be preferably formed using the same materials as the non-conductive materials forming the main body.

The second supporting member 72b has a projecting part 72f corresponding to the ring-shaped conductive band 52c. Also, the first supporting member 72a and the second supporting member 72b have the structures 72d, 72e suitable to fit into each other, for example the joint structure between prominence and depression. Namely, the first supporting member 72a has a T-shaped depression 72d sticking in and the second supporting member 72b has a T-shaped prominence part 72e sticking out. Other structures that will fix the two parts in place might be applied. The first supporting member 72a has a cylindrical sleeve through which the electrical cable including multiple electrical lines passes and an opening 72c that guides the electrical lines to the outside of the supporting member.

Then as shown in FIG. 7B, the second supporting member 72b is placed inside the ring-shaped conductive bands enclosing the ring-shaped metal bands connected to the wires, while the ring-shaped conductive bands are arranged apart from each other by a predetermined distance.

As shown in FIG. 7C, the electrical cable passes through the sleeve. The first and the second supporting members 72a and 72b are put together then the electrical cable is fastened.

Figure 7D:
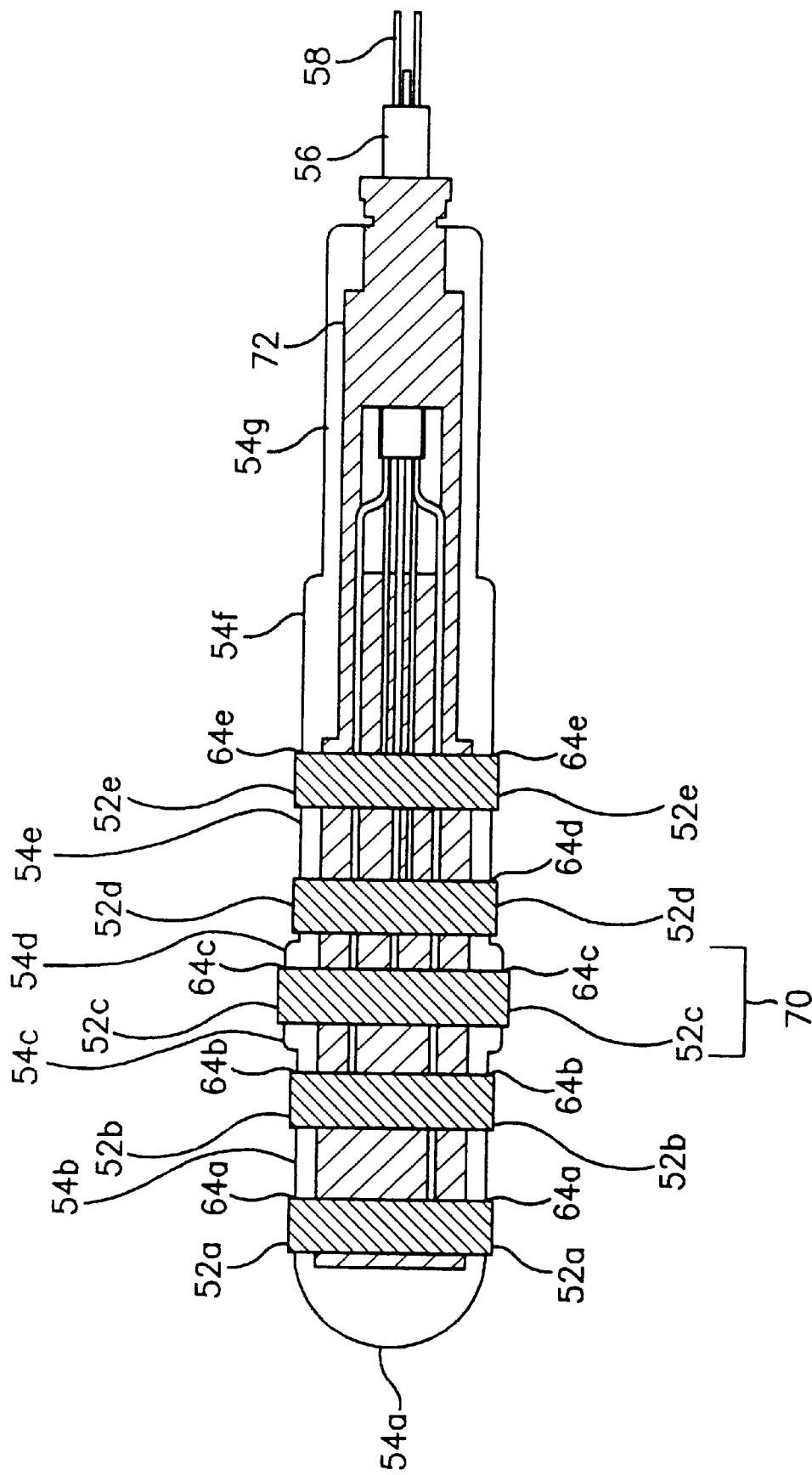

Afterwards, the fixed parts up to the above step are mounted in the cylindrical matrix as shown in FIG. 7D, and non-conductive materials such as non-conductive silicon is filled and molded in between the ring-shaped conductive bands 52a, 52b, 52c, 52d, 52e. Thus, the supporting members 72a and 72b are merged into the main body.

As described in FIG. 7, using the supporting members to manufacture electrodes for insertion into a body cavity is not only convenient but also effective in reducing the manufacturing of defective products. In addition, the first and second supporting members can be manufactured by molding, which is very inexpensive. In result, it reduces the manufacturing time and costs of electrodes. Compared to the existing methods, the manufacturing method of the present invention can reduce the manufacturing costs by 90%.

Differently from what was explained in FIGS. 7A and 7D, it is possible to form an electrode for insertion into a body cavity with only one supporting member. In such a case, it is desirable to form the supporting member substantially in the same manner as the second supporting member 72b.

In addition, it is possible to form an electrode for insertion into a body cavity with three or more supporting members.

Figure 8:
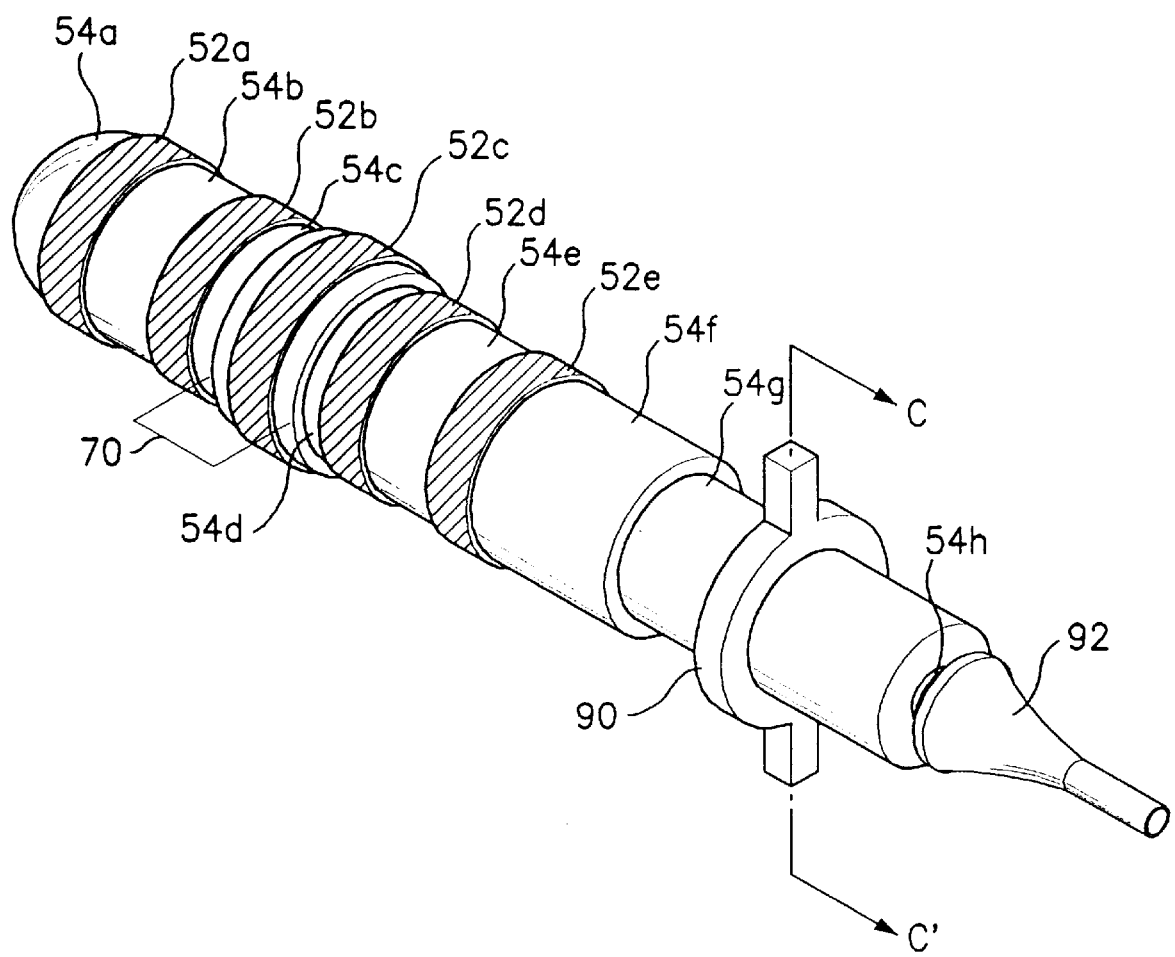
FIG. 8 is a perspective view of a third embodiment of an electrode for insertion into a body cavity.

FIG. 8 is a perspective view of a third embodiment of an electrode for insertion into a body cavity.

Referring to FIG. 8, the electrode for insertion into a body cavity of the present invention is supplied with an insertion-depth control member 90 and electrical line protector 92. The insertion-depth control member 90 is used together with the main body and can be made of materials of a high frictional resistance against the materials constituting the main body, such as plastic. And the frictional resistance should be just enough so that the insertion-depth control member can be moved along the length of the electrode by hand before being inserted into the patient's body cavity.

The insertion-depth control member, while the electrode is being inserted into a body cavity, stays outside the body cavity.

As shown in FIG. 8, the electrical line protector 92 is attached to the sleeve of the rear side of the electrode for insertion into a body cavity, and should be made of materials that is firmer than the materials constituting the main body.

Figure 9:
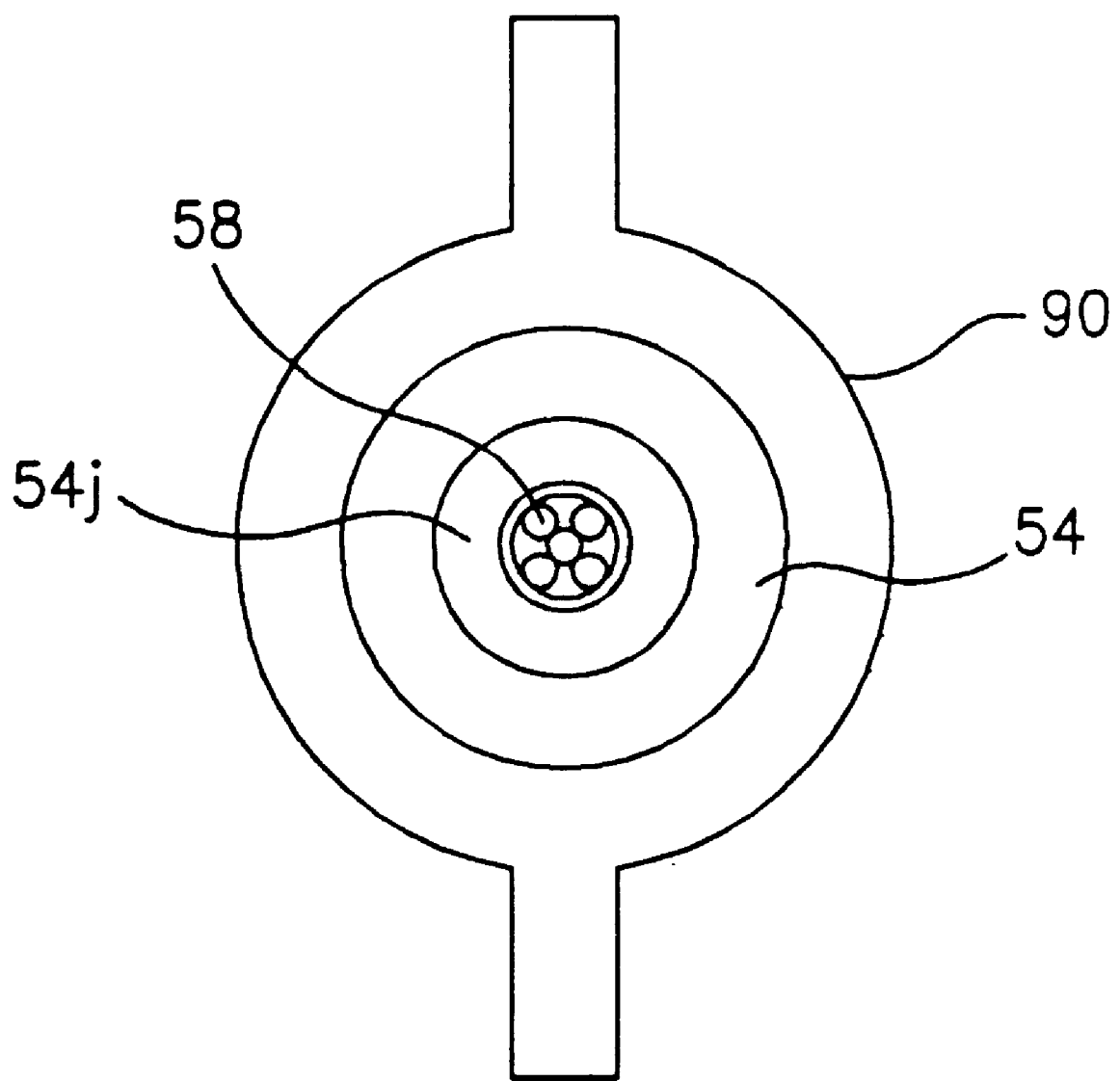
FIG. 9 is a sectional view of the electrode taken along line C–C' of FIG. 8.

FIG. 9 is a sectional view of the electrode taken along line C–C' of FIG. 8, and the inner diameter of the insertion depth control member 90 should be substantially the same as the outer diameter of the main body.

The electrode for insertion into a body cavity described so far can be utilized not only for treatment for urinary incontinence, but also treatment for constipation, fecal incontinence, and for low-frequency physical therapy, EMG signal measurement, muscle stimulation treatment and bladder impedance measurement.

As described above, the electrode for insertion into a body cavity of the present invention can be manufactured very easily and cost-effectively, and very comfortable to insert if made of silicon.

In addition, the adhesion of the conductive, non-conductive bands and electrical lines is very firm; thus the main body is very solid and resistant to external mechanical impacts. The insertion-depth control member 90 has an advantage in that it can control the depth of insertion according to the length of the body cavity of the patient.

Although the present invention has been described with reference to preferred embodiments, those skilled in the art will appreciate that changes may be made in form and detail without departing from the spirit and scope of the invention.

What is claimed is:

1. An electrode for medical treatment purposes which may be inserted into a body cavity and used in contact with a muscular surface, and through which at least one electrical signal is applied to the muscular surface under a control of a controller and at least one EMG signal is detected from the muscular surface, said electrode comprising:

a rod-shaped main body composed of non-conductive material;

a plurality of ring-shaped conductive bands each of which is disposed apart from one another along a longitudinal axis of said rod-shaped main body;

a plurality of ring-shaped metal bands each of which is buried within one of said plurality of ring-shaped conductive bands, respectively; and a plurality of electrical lines each of which has one end connected to a corresponding one of said plurality of ring-shaped metal bands and buried within said rod-shaped main body and the other end extended through a rear side of said rod-shaped main body to be electrically coupled to the controller.

2. The electrode of claim 1, wherein said rod-shaped main body is made of non-conductive silicon.

3. The electrode of claim 1, wherein said ring-shape conductive bands are made of conductive silicon.

4. The electrode of claim 3, wherein each of said ring-shaped conductive bands has been formed thicker in comparison with adjacent parts of said main body.

5. The electrode of claim 4, wherein each of said ring-shape conductive bands has a radius larger than that of an outer surface of said main body by 0.1 to 0.3 mm.

6. The electrode of claim 5, which has a thick middle part to prevent dislocation of said rod-shaped main body.

7. The electrode of claim 6, wherein at least one of said ring-shaped conductive bands is located on the thick middle part.

8. The electrode of claim 7, wherein said ring-shaped conductive band located on the thick middle part is coupled to a ground potential.

9. The electrode of claim 3, wherein the conductivity of said conductive silicon is 5–20Ω.cm.

10. The electrode of claim 3, wherein the width of said ring-shaped conductive band is 3–15 mm.

11. The electrode of claim 10, wherein said conductive bands are separated from each other by 2–20 mm.

12. The electrode of claim 1, wherein the electrode is a vaginal electrode for treatment of urinary incontinence treatment.

13. The electrode of claim 12, wherein the solidity of said rod-shaped of main body is 30–80 Shore A.

14. The electrode of claim 12, wherein the diameter of said ring-shaped main body is 15–30 mm and the length is 80–135 mm.

15. The electrode of claim 1, wherein a front side of the main body is formed in dome-shaped.

16. The electrode of claim 1, further comprising an electrical line-protecting member at the rear side of said rod-shaped main body.

17. The electrode of claim 1, further comprising an insertion-depth control member, which can be coupled to the rear side of, said main body so as to control the depth of insertion into a body cavity.

18. The electrode of claim 1, wherein said rod-shaped main body is comprised of a plastic material.

19. The electrode of claim 1, wherein said ring-shaped conductive bands are comprised of a metal.

20. A manufacturing method of an electrode for insertion into a body cavity during medical treatment, comprising the steps of:

forming a plurality of ring-shaped metal bands;

forming a plurality of ring-shaped conductive bands at the inner and/or outer circumferences of said plurality of ring-shaped metal bands by a molding process using conductive material;

soldering a plurality of electrical lines to the plurality of ring-shaped metal bands, respectively;

disposing the plurality of conductive bands including the ring-shaped metal bands coupled to the electrical lines in the longitudinal direction on a rod-shape matrix and arranging the electrical lines such that one ends of the electrical lines are extended through one end of said rod-shaped matrix to outside of the matrix; and molding the non-conductive material in between and inside of said ring-shaped conductive bands in the matrix, so as to form the electrode.

21. The manufacturing method of said electrode of claim 20, wherein said plurality of ring-shaped conductive bands is molded by using conductive silicon and said non-conductive material is non-conductive silicon.

22. A manufacturing method of an electrode for insertion into a body cavity during medical treatment, comprising the steps of:

forming a plurality of ring-shaped metal bands;

forming a plurality of ring-shaped conductive bands by molding conductive material in the inner and outer surface of said ring-shaped metal bands;

soldering a plurality of electrical lines to said ring-shaped metal bands, respectively;

molding non-conductive material into a supporting member;

inserting the supporting member into the plurality of ring-shaped conductive bands including the ring-shaped metal bands coupled to the electrical lines such that the ring-shaped conductive bands are disposed apart from one another;

mounting said supporting member inserted into said plurality of conductive bands on a rod-shaped matrix and arranging the electrical lines such that one ends of the electrical lines are extended through one end of the rod-shaped matrix to outside of the matrix; and molding non-conductive material in between and inside of said ring-shaped conductive bands in the matrix, so as to form the electrode.

23. The manufacturing method of claim 22, wherein said conductive material is conductive silicon and said non-conductive material is non-conductive silicon.

24. The manufacturing method of claim 22, wherein said conductive material is comprised of a plastic material and said non-conductive material is comprised of a metal.

25. A manufacturing method of an electrode for insertion into a body cavity during medical treatment, comprising the steps of:

forming a plurality of ring-shaped metal bands;

forming a plurality of ring-shaped conductive bands by molding conductive material in the inner and outer surface of said ring-shaped metal bands;

soldering a plurality of electrical lines to said ring-shaped metal bands, respectively;

molding a first non-conductive material into a first and a second supporting members, wherein said first and said second supporting members have structures suitable to fit into each other and said first supporting member includes an electrical line guide opening;

inserting the second supporting member into the plurality of ring-shaped conductive bands including the ring-shaped metal bands coupled to the electrical lines such that the ring-shaped conductive bands are disposed apart from one another;

making the electrical lines pass through the electrical line guide opening of said first supporting member;

coupling the first and the second supporting members together;

mounting said resulting produce on a rod-shaped matrix; and molding a second non-conductive material in between and inside of said ring-shaped conductive bands in the matrix, so as to form the electrode.

26. The manufacturing method of claim 25, wherein said first and second non-conductive materials are the same materials.

27. The manufacturing method of claim 26, wherein said first and second non-conductive materials are non-conductive silicon.

28. The manufacturing method of claim 25, wherein said conductive material is conductive silicon.

* * * * *